United States Patent [19]

Merger et al.

[11] Patent Number: 4,963,673

[45] Date of Patent: Oct. 16, 1990

[54] PREPARATION OF CAPROLACTAM

[75] Inventors: Franz Merger, Frankenthal; Rolf Fischer, Heidelberg; Claus-Ulrich Priester, Ludwigshafen, all of Fed. Rep. of Germany

[73] Assignee: BASF Aktiengesellschaft, Ludwigshafen, Fed. Rep. of Germany

[21] Appl. No.: 448,902

[22] Filed: Dec. 12, 1989

[51] Int. Cl.$^5$ ............................................. C07D 201/08
[52] U.S. Cl. ..................................................... 540/538
[58] Field of Search ............................................ 540/535

[56] References Cited

U.S. PATENT DOCUMENTS

| | | | |
|---|---|---|---|
| 3,857,510 | 12/1974 | Rogic et al. | 540/538 |
| 4,730,041 | 3/1988 | Hutmacher et al. | 540/538 |
| 4,731,445 | 3/1988 | Hutmacher et al. | 540/538 |
| 4,767,856 | 7/1988 | Dockner et al. | 540/538 |
| 4,767,857 | 8/1988 | Merger et al. | 540/538 |

FOREIGN PATENT DOCUMENTS

| | | | |
|---|---|---|---|
| 2249993 | 4/1973 | Fed. Rep. of Germany | 540/538 |
| 3643010 | 6/1988 | Fed. Rep. of Germany | 540/538 |
| 3643911 | 6/1988 | Fed. Rep. of Germany | 540/538 |

*Primary Examiner*—Robert T. Bond
*Attorney, Agent, or Firm*—Keil & Weinkauf

[57] ABSTRACT

Caprolactam is prepared by heating a 6-aminocaproic ester in liquid phase in the presence of water to 230°–350° C. under superatmospheric pressure in a reaction medium comprising a liquid aromatic hydrocarbon having a boiling point of from 80° to 240° C. which is inert under reaction conditions, and isolating caprolactam from the reaction mixture.

10 Claims, No Drawings

PREPARATION OF CAPROLACTAM

The present invention relates to a process for preparing caprolactam from 6-aminocaproic esters.

DE-A- No. 2,249,993 describes a process wherein 6-aminocaproic esters are converted in the presence of water at from 250° to 350° C. into caprolactam. However, the process has the disadvantage that, as is known from Industrial Engineering Chem. Proc. Design Development 17 (1978), 11, this reaction proceeds via 6-aminocaproic acid and therefore, as is evident from page 15, the cyclization should be carried out at low concentrations in order to suppress the formation of oligomers. As a consequence, it becomes technically complicated to isolate the caprolactam from the dilute aqueous solutions.

DE-A- No. 3,643,010 describes the cyclization of 6-aminocaproic esters to caprolactam in aromatic hydrocarbons having a boiling point of from 80° to 240° C. as reaction medium at from 100° to 320° C. However, the reaction requires residence times of up to 15 hours. The reaction rate and the space-time yields are so low as to be in need of improvement for industrial practice of the process.

Equally, the process described in DE-A- No. 3,643,011 for preparing caprolactam by cyclization of 6-aminocaproic esters at from 150° to 350° C. in a liquid reaction medium which is inert under reaction conditions and which has a boiling point above that of caprolactam, the products caprolactam and alkanol being continuously removed from the reaction mixture at their rate of formation, gives a space-time yield which is in need of improvement.

It is an object of the present invention to provide a process for preparing caprolactam from 6-aminocaproic esters which proceeds with high selectivity and high conversion in an industrially satisfactory space-time yield and which minimizes the formation of by-products.

We have found that this object is achieved by a process for preparing caprolactam, which comprises heating a 6-aminocaproic ester in liquid phase in the presence of water to 230°–350° C. under superatmospheric pressure in a reaction medium comprising a liquid aromatic hydrocarbon having a boiling point of from 80° to 240° C. which is inert under reaction conditions, and isolating caprolactam from the reaction mixture.

The novel process has the advantage of giving improved space-time yields and high conversions and selectivities. Furthermore, the novel process has the advantage that, despite the presence of water, the formation of by-products is avoided.

Preferred starting materials are 6-aminocaproic esters of alkanols of from 1 to 10 carbon atoms, cycloalkanols of from 5 to 8 carbon atoms or aralkanols of from 7 to 10 carbon atoms. Suitable starting materials are for example methyl, ethyl, isopropyl, n-propyl, cyclohexyl and benzyl 6-aminocaproates. Particular preference is given to alkyl 6-aminocaproates, in particular $C_1$–$C_4$-alkyl 6-aminocaproates. Particular industrial importance has been attained by methyl 6-aminocaproate and ethyl 6-aminocaproate.

According to the invention, the reaction medium used is a liquid aromatic hydrocarbon having a boiling point of from 80° to 240° C., in particular from 110° to 200° C., which is inert under reaction conditions. Preferred aromatic hydrocarbons are alkylbenzenes, in particular those which contain from 1 to 3 alkyl groups of up to 6 carbon atoms. Particular preference is given to alkylbenzenes having from 1 to 3 alkyl radicals with up to 4 carbon atoms in total. Suitable aromatic hydrocarbons are for example benzene, toluene, xylenes, ethylbenzene, diethylbenzene, trimethylbenzene, isopropylbenzene, propylbenzene and diisopropylbenzene. Particular preference is given to toluene and the xylenes.

In general, from 2 to 20, in particular from 4 to 15, kg of aromatic hydrocarbon is used per kg of aminocaproic ester. Particular preference is given to the range from 5 to 12 kg of aromatic hydrocarbon per kg of 6-aminocaproic ester.

According to the invention, the reaction is carried out in the presence of water. In general, from 1 to 10 moles of water are used per mole of 6-aminocaproic ester. It is particularly advantageous to use from 1.5 to 6 moles, in particular from 2 to 4 moles, of water per mole of 6-aminocaproic ester.

The reaction is carried out at from 230° to 350° C., advantageously at from 260° to 340° C.

The temperature and pressure conditions are selected in such a way that the reaction mixture is always present in the liquid state. Advantageously, a pressure of from 30 to 200 bar, in particular from 40 to 110 bar, is employed.

Advantageously, the reaction is carried out with a residence time of from 5 to 60 minutes, in particular from 7 to 45 minutes. The range from 10 to 20 minutes is particularly advantageous.

The mixture of 6-aminocaproic ester, water and aromatic hydrocarbon is heated to the specified temperature under pressure and temperature conditions, as mentioned, selected in such a way that the reaction mixture is in the liquid state. The reaction can be carried out batchwise, for example in pressure vessels. Preferably, however, the reaction is carried out continuously, for example in pressure vessel cascades, for example in from 2 to 4 consecutive pressure vessels. It is particularly advantageous to carry out the reaction in a tubular reaction zone. Suitable reaction zones have for example a length:diameter ratio of from 100:1 to 10,000:1. It is advantageous here to emulsify the starting materials, e.g. a solution of 6-aminocaproic ester in an aromatic hydrocarbon and water, advantageously at from −10° to +20° C., and then to introduce the emulsion into the tube reactor.

The resulting solution of caprolactam in an aromatic hydrocarbon is in general subjected to fractional distillation to isolate the caprolactam and to recycle the aromatic hydrocarbon. In a preferred procedure, however, caprolactam is extracted with water from the aromatic hydrocarbon. Advantageously, the extraction is carried out in countercurrent in known apparatus, e.g. mixer/settlers, stirred disk columns or sieve plate columns with or without pulsation. Advantageously, the extraction is carried out from 20° to 80° C. It is advantageous here to purify a bleed stream of the aromatic hydrocarbon by distillation before reuse.

The caprolactam is suitable for preparing polycaprolactam, an important fiber raw material.

The process according to the present invention is illustrated by the following Examples:

EXAMPLE 1

251.0 ml (220.0 g) of a solution of 8.80% by weight (19.36 g, 0.134 mol) of methyl 6-aminocaproate and 0.16% by weight of caprolactam (0.36 g, 0.003 mol) in o-xylene and 14.4 ml (0.80 mol) of water are recirculated per hour through a 70 ml tube reactor having an internal diameter of 2.2 mm and a length of 18.4 m at 100 bar and 270° C. with a residence time of 15.8 minutes. The reaction solution is depressurized to atmospheric via an overflow valve, homogenized with methanol and analyzed by quantitative gas chromatography. Besides 0.57 g of unconverted methyl 6-aminocaproate (conversion: 97.1%) it is found to contain 14.50 g (selectivity: 96.6%) of caprolactam.

EXAMPLE 2

265.6 ml (232.8 g) of a solution of 8.96% by weight (20.86 g, 0.144 mol) of methyl 6-aminocaproate and 0.17% by weight of caprolactam (0.40 g, 0.004 mol) in o-xylene and 10.8 ml (0.60 mol) of water are recirculated per hour through a 70 ml tube reactor having an internal diameter of 2.2 mm and a length of 18.4 m at 100 bar and 70° C. with a residence time of 15.2 minutes. The reaction solution is depressurized to atmospheric via an overflow valve, homogenized with methanol and analyzed by quantitative gas chromatography. Besides 1.03 g of unconverted methyl 6-aminocaproate (conversion: 95.1%) it is found to contain 14.33 g (selectivity: 90.1%) of caprolactam.

EXAMPLE 3

224.0 ml (196.4 g) of a solution of 8.94% by weight (17.56 g, 0.121 mol) of methyl 6-aminocaproate and 0.17% by weight of caprolactam (0.33 g, 0.003 mol) in o-xylene and 9.6 ml (0.53 mol) of water are recirculated per hour through a 70 ml tube reactor having an internal diameter of 2.2 mm and a length of 18.4 m at 100 bar and 270° C. with a residence time of 18.0 minutes. The reaction solution is depressurized to atmospheric via an overflow valve, homogenized with methanol and analyzed by quantitative gas chromatography. Besides 0.46 g of unconverted methyl 6-aminocaproate (conversion: 97.4%) it is found to contain 12.45 g (selectivity: 90.9%) of caprolactam.

EXAMPLE 4

260.0 ml (228.9 g) of a solution of 8.53% by weight (19.53 g, 0.135 mol) of methyl 6-aminocaproate and 0.17% by weight of caprolactam (0.39 g, 0.003 mol) in o-xylene and 8.3 ml (8.1 g) of a solution of 5.19% by weight (0.42 g) of methyl 6-aminocaproate and 3.21% by weight of caprolactam (0.26 g) in water are pumped per hour through a 70 ml tube reactor having an internal diameter of 2.2 mm and a length of 18.4 m at 100 bar and 270° C. with a residence time of 15.7 minutes. The reaction solution is depressurized to atmospheric via an overflow valve and concentrated under the reduced pressure of a rotary evaporator for an hour. According to quantitative gas chromatography, the residue contains 0.61 g of methyl 6-aminocaproate (conversion: 96.9%) and 14.95 g (selectivity: 94.9%) of caprolactam.

EXAMPLE 5

264.7 ml (234.1 g) of a solution of 8.50% by weight (19.90 g, 0.137 mol) of methyl 6-aminocaproate and 0.16% by weight of caprolactam (0.37 g, 0.003 mol) in o-xylene and 8.9 ml (8.9 g) of a solution of 7.53% by weight (0.67 g) of methyl 6-aminocaproate and 4.61% by weight of caprolactam (0.41 g) in water are pumped per hour through a 70 ml tube reactor having an internal diameter of 2.2 mm and a length of 18.4 m at 100 bar and 70° C. with a residence time of 15.4 minutes. The reaction solution is depressurized to atmospheric via an overflow valve, homogenized with methanol and analyzed by quantitative gas chromatography. Besides 0.2 g of unconverted methyl 6-aminocaproate (conversion: 98.0%) it is found to contain 14.74 g (selectivity: 88.9%) of caprolactam.

EXAMPLE 6

367.1 g of a solution of 9.31% by weight (34.19 g, 0.236 mol) of methyl 6-aminocaproate and 0.32% by weight (1.19 g, 0.011 mol) of caprolactam in o-xylene and 15.9 g (0.88 mol) of water are emulsified in a jacketed flask temperature controlled to 0° C., and the emulsion is pumped from there at 70 bar at 300° C. through a 70 ml tube reactor with a residence time of 10 minutes. The reactor is then rinsed with 100 ml of xylene, and the collected portions are concentrated in a rotary evaporator under reduced pressure, leaving 36.9 g of product which according to quantitative analysis by gas chromatography contains 6.37% of methyl 6-aminocaproate (2.35 g, conversion: 93.1%) and 64.88% (23.94 g, selectivity: 91.7%) of caprolactam.

EXAMPLE 7

463.0 g of a solution of 9.32% by weight (43.15 g, 0.298 mol) of methyl 6-aminocaproate and 0.27% by weight (1.26 g, 0.011 mol) of caprolactam in o-xylene and 19.7 g (1.09 mol) of water are emulsified in a jacketed flask temperature controlled to 0° C., and the emulsion is pumped from there at 70 bar at 330° C. through a 70 ml tube reactor with a residence time of 10 minutes. The reactor is then rinsed with 100 ml of xylene, and the collected portions are concentrated in a rotary evaporator under reduced pressure, leaving 47.8 g of product which according to quantitative analysis by gas chromatography contains 3.99% of methyl 6-aminocaproate (1.91 g, conversion: 95.6%) and 63.23% (30.22 g, selectivity: 0.1%) of caprolactam.

EXAMPLE 8

669.5 g of a solution of 10.26% by weight (68.70 g, 0.474 mol) of methyl 6-aminocaproate and 0.32% by weight (2.17 g, 0.019 mol) of caprolactam in o-xylene and 10.0 g (0.56 mol) of water are emulsified in a jacketed flask temperature controlled to 0° C., and the emulsion is pumped from there at 70 bar at 270° C. through a 70 ml tube reactor with a residence time of 11.7 minutes. The reactor is then rinsed with 70 ml of xylene, and the collected portions are concentrated in a rotary evaporator under reduced pressure, leaving 72.3 g of product which according to quantitative analysis by gas chromatography contains 5.80% of methyl 6-aminocaproate (4.20 g, conversion: 93.9%) and according to quantitative HPLC 77.7% (49.01 g, selectivity: 93.2%) of caprolactam.

EXAMPLE 9

591.1 g of a solution of 22.27% by weight (131.62 g, 0.908 mol) of methyl 6-aminocaproate and 0.65% by weight (3.84 g, 0.033 mol) of caprolactam in o-xylene and 17.7 g (0.98 mol) of water are emulsified in a jacketed flask temperature controlled to 0° C., and the emulsion is pumped from there at 70 bar at 270° C. through a 70 ml tube reactor with a residence time of 11.7 minutes. The reactor is then rinsed with 70 ml of xylene, and the collected portions are concentrated in a rotary evaporator under reduced pressure, leaving 104.2 g of product which according to quantitative analysis by gas chromatography contains 0.34% of methyl 6-aminocaproate (0.35 g, conversion: 99.7%) and 90.06% (93.84 g, selectivity: 88.0%) of caprolactam.

EXAMPLE 10

416.1 g of a solution of 19.95% by weight (83.00 g, 0.572 mol) of methyl 6-aminocaproate and 0.53% by weight (2.19 g, 0.019 mol) of caprolactam in o-xylene and 22.2 g (1.23 mol) of water are emulsified in a jacketed flask temperature controlled to 0° C., and the emulsion is pumped from there at 70 bar at 270° C. through a 70 ml tube reactor with a residence time of 8.4 minutes. The exit stream is homogenized with methanol. According to quantitative analysis by gas chromatography, 61.8 g of caprolactam (yield: 92.2%) are formed.

EXAMPLE 11

A mixture of 9.97% by weight of methyl 6-aminocaproate, 0.09% by weight of caprolactam, 1.3% by weight of water and 88.64% by weight of o-xylene is emulsified in a jacketed flask temperature controlled to 0° C., and pumped from there at 40 bar and 270° C. through a 70 ml tube reactor with residence times of from 9.5 to 43 minutes. The exit streams are homogenized with methanol an analyzed by quantitative gas chromatography.

| Run | Residence time [min.] | Conversion [%] | Selectivity [%] |
|---|---|---|---|
| A | 9.5 | 91.9 | 94.2 |
| B | 14 | 94.5 | 91.1 |
| C | 43 | 100 | 97.4 |

COMPARATIVE EXAMPLE 1

A solution of 9.55% by weight of methyl 6-aminocaproate and 0.27% by weight of caprolactam in o-xylene is pumped at 40 bar and 270° C. through a 70 ml tube reactor with a residence time of from 11 to 44 minutes. The exit streams are analyzed by quantitative gas chromatography.

| Run | Residence time [min.] | Conversion [%] | Selectivity [%] |
|---|---|---|---|
| A | 11 | 49.8 | 80.9 |
| B | 25 | 77.2 | 80.7 |
| C | 33.5 | 91.9 | 81.7 |
| D | 44 | 98.7 | 82.9 |

COMPARATIVE EXAMPLE 2

A solution of 15 g (0.0943 mol) of ethyl 6-aminocaproate in 45 ml of water was heated from 15° to 270° C. in a 0.25 l shaker autoclave in the course of 3 hours and subsequently shaken at that temperature under autogenous pressure (52-65 bar) for 1 hour. Cooling down to room temperature, extraction with trichloromethane (5 times 20 ml), drying over sodium sulfate and concentrating under reduced pressure left 8 g of crude caprolactam (purity according to GC: 94%) having a melting point of from 66° to 67° C., which corresponds to a yield of 70.5%.

COMPARATIVE EXAMPLE 3

A solution of 20 g (0.126 mol) of ethyl 6-aminocaproate in 60 ml of water was heated from 20° to 300° C. in a 0.25 l shaker autoclave in the course of 5.5 hours and subsequently shaken at that temperature under autogenous pressure (80-85 bar) for 15 minutes. Cooling down to room temperature, extraction with trichloromethane (5 times 50 ml), drying over sodium sulfate and concentrating under reduced pressure left 11.3 g of crude caprolactam having a melting point of from 65° to 68° C., which corresponds to a yield of 79.4%.

COMPARATIVE EXAMPLE 4

A solution of 20 g (0.126 mol) of ethyl 6-aminocaproate in 60 ml of water was heated to 300° C. in a 0.25 l shaker autoclave in the course of 5.5 hours and subsequently shaken at that temperature under autogenous pressure (60-90 bar) for 1 hour. Cooling down to room temperature, extraction with trichloromethane (7 times 20 ml), drying over sodium sulfate and concentrating under reduced pressure left 11.9 g of crude caprolactam having a melting point of from 64° to 66° C., which corresponds to a yield of 83.6%.

COMPARATIVE EXAMPLE 5

A solution of 30.8 g (0.212 mol) of methyl 6-aminocaproate and 4.8 g (0.042 mol) of caprolactam in 112.5 g of water were heated to 300° C. in a 375 ml stirred autoclave in the course of one hour, resulting in an autogenous pressure of 80 bar. At that stage the reaction solution was found to contain by quantitative gas chromatography 15.38% by weight of caprolactam (corresponding to a yield of 76%, based on methyl 6-aminocaproate and also 0.57% of N-methylcaprolactam.

COMPARATIVE EXAMPLE 6

A solution of 18.28% of methyl 6-aminocaproate and 5.75% of caprolactam in water was pumped through a 40 ml tube reactor at 300° C. and 100 bar with a residence time of 15 minutes. The exit stream contained according to quantitative gas chromatography 15.09% by weight of caprolactam, corresponding to a yield of 65.6%, based on methyl 6-aminocaproate. N-methylcaprolactam was formed as a by-product in a 5.8% yield.

COMPARATIVE EXAMPLE 7

A solution of 15.7% of methyl 6-aminocaproate and 8.2% of caprolactam in water was pumped through a 40 ml tube reactor at 270° C. and 100 bar with a residence time of 4.2 minutes. The exit stream contained according to quantitative gas chromatography 14.98% by weight of caprolactam, corresponding to a yield of 55.4%, based on methyl 6-aminocaproate. N-methylcaprolactam was formed as a by-product in a 4.5% yield.

We claim:

1. A process for preparing caprolactam, which comprises heating a 6-aminocaproic ester in liquid phase in the presence of water to 230°-350° C. under superatmospheric pressure in a reaction medium comprising a liquid aromatic hydrocarbon having a boiling point of from 80° to 240° C. which is inert under reaction conditions, and isolating caprolactam from the reaction mixture.

2. A process as claimed in claim 1, wherein 260°-340° C. is maintained.

3. A process as claimed in claim 1, wherein 30-200 bar is maintained.

4. A process as claimed in claim 1, wherein from 1 to 10 moles of water are used per mole of 6-aminocaproic ester.

5. A process as claimed in claim 1, wherein a residence time of from 5 to 60 minutes is maintained.

6. A process as claimed in claim 1, wherein an alkylbenzene having a boiling point of from 110° to 200° C. is used.

7. A process as claimed in claim 1, wherein toluene or xylene is used.

8. A process as claimed in claim 1, wherein the reaction is carried out in a tubular reaction zone.

9. A process as claimed in claim 1, wherein the 6-aminocaproic ester, the aromatic hydrocarbon and the water are emulsified at from −10° to +20° C. before the reaction.

10. A process as claimed in claim 1, wherein a $C_1$–$C_4$-alkyl 6-aminocaproate is used.

* * * * *

UNITED STATES PATENT AND TRADEMARK OFFICE
CERTIFICATE OF CORRECTION

PATENT NO. : 4,963,673

DATED : October 16, 1990

INVENTOR(S) : Franz MERGER et al.

It is certified that error appears in the above-identified patent and that said Letters Patent is hereby corrected as shown below:

ON THE COVER PAGE insert

-- Foreign Application Priority Data

[DE] Federal Republic of Germany    3843793    December 24, 1988 --

Signed and Sealed this

Fourteenth Day of January, 1992

Attest:

HARRY F. MANBECK, JR.

Attesting Officer

Commissioner of Patents and Trademarks